United States Patent [19]
Silber et al.

[11] Patent Number: 5,928,154
[45] Date of Patent: Jul. 27, 1999

[54] ULTRASOUND PROBE HOUSING WITH REDUCED CONTROL PRESSURE GRIP AND METHOD FOR MANUFACTURING SAME

[75] Inventors: Daniel A. Silber, Lexington; Brevard S. Garrison, Reading; Susan Williams, Tyngsboro, all of Mass.

[73] Assignee: Hewlett-Packard Company, Palo Alto, Calif.

[21] Appl. No.: 09/056,910

[22] Filed: Apr. 8, 1998

[51] Int. Cl.⁶ ..................................................... A61B 8/00
[52] U.S. Cl. ............................................................ 600/459
[58] Field of Search .................................. 600/446, 459, 600/121; 128/916

[56] References Cited

U.S. PATENT DOCUMENTS

| | | |
|---|---|---|
| 4,246,444 | 1/1981 | Mason . |
| 4,476,742 | 10/1984 | Midgley . |
| 4,934,024 | 6/1990 | Sexton . |
| 5,155,878 | 10/1992 | Dellis . |
| 5,390,572 | 2/1995 | Gakhar et al. . |
| 5,404,267 | 4/1995 | Silva et al. . |
| 5,446,941 | 9/1995 | Kelsay . |
| 5,499,422 | 3/1996 | Lavazoli . |
| 5,554,098 | 9/1996 | Yabe et al. ............................... 600/121 |
| 5,690,113 | 11/1997 | Sliwa, Jr. et al. ........................ 128/916 |
| 5,810,733 | 9/1998 | Van Creveld et al. .................. 600/459 |

OTHER PUBLICATIONS

Beere Precision Medical Instruments, Ortho–Grip® Product Information 1996.

*Primary Examiner*—Marvin M. Lateef
*Assistant Examiner*—Ali M. Imam

[57] ABSTRACT

A grip layer formed circumferentially around a substantial portion of a length of an ultrasound probe housing and having a high coefficient of friction. The grip layer enables an administering sonographer to maintain control over the ultrasound probe during transthoracic and other ultrasound imaging procedures while applying minimal gripping force. Furthermore, the grip layer accommodates all ultrasound viewing windows regardless of the position of the patient, the location of the sonographer relative to the patient and whether the sonographer uses a right- or left-handed technique. The grip layer is joined to an inner housing so as to form a gas- and liquid-impermeable seal between the grip layer and inner housing, enabling the ultrasound probe to withstand repeated applications of autoclaving, liquid and chemical disinfecting and other sterilization procedures without compromising the electrical integrity of the probe casing. The grip layer and inner housing form a continuously smooth casing surface that is substantially impenetrable by cleaning solvents, coupling gel or contaminants. The grip layer is preferably a substantially thin, non-compressible, elastomeric coating having a low durometer, high chemical resistance and good cut resistance. The grip layer is preferably a thermoplastic elastomer.

23 Claims, 3 Drawing Sheets

ULTRASOUND PROBE HOUSING WITH REDUCED CONTROL PRESSURE GRIP AND METHOD FOR MANUFACTURING SAME

BACKGROUND OF THE INVENTION

1. Field of the Invention

The present invention relates generally to ultrasonic probes and, more particularly, to transthoracic ultrasound imaging probes.

2. Related Art

The use of ultrasound for medical imaging is well-known. Since its introduction, advances in technology and clinical practice have made ultrasound a leading medical diagnostic imaging modality. Ultrasound provides high-resolution real-time imaging without the use of ionizing radiation which is required for other techniques such as X-ray imaging. In addition, modern ultrasound equipment is relatively inexpensive and portable. This cost-effectiveness and portability has resulted in the widespread application of ultrasound imaging to observe a wide range of physical conditions and to identify many types of disorders.

For example, ultrasound imaging is commonly used in surgical and intravascular applications, as well as in guiding other interventional procedures. In addition, ultrasound is used in such clinical applications as obstetrics and gynecology, general abdominal imaging, vascular imaging and cardiology. This latter application, which is of significance in the present application, is referred to as echocardiography.

Various techniques have been developed for ultrasound cardiac imaging. Some conventional methods include invasive steps in which there is some disruption or alteration of the vascular and/or cardiac systems. Other conventional methods are directed to imaging the heart during surgical operations when the heart is exposed. These invasive approaches are limited in their application for a variety of reasons, including patient discomfort, increased risk of complications, and the need to use sterilized and expensive medical devices.

Non-invasive echocardiographic methods also exist. Conventional transthoracic ultrasound imaging probes have been developed for this purpose primarily because surgical imaging probes were found to be inappropriate for use in non-invasive or transthoracic cardiac imaging. The acoustical energy generated by the small transducers of invasive imaging probes is generally insufficient to penetrate the body and intervening anatomical structures.

Conventional transthoracic ultrasound imaging probes are generally elongate probes having an ultrasound transducer located on the distal end of the probe body. The probes are generally constructed of a hard plastic casing to facilitate cleaning of the probes. Typically, the probe is maneuvered so that the transducer is positioned adjacent to an external location on the body where acoustic imaging is facilitated by the underlying tissue. In cardiac imaging, these locations, referred to as an imaging windows, are typically between the ribs of the patient.

There are four primary echocardiographic imaging windows: the suprasternal, subcostal, parasternal and apical windows. The appropriateness of each imaging window depends upon the structures, functions and conditions to be diagnosed as well as the type and size of the patient. Each imaging window provides an opportunity to image a specific portion or characteristic of the cardiac structures and/or functions depending on the portion of the heart which is nearest the imaging window, the angle of the probe at that window, and the intervening structures which may interfere with imaging the desired cardiac structures. In addition, the utility of certain windows is limited by the size and condition of the patient. Accordingly, specific windows are used to diagnose specific conditions and disorders of specific patients.

When performing transthoracic echocardiographic procedures, the patient is generally lying horizontally on his or her left side. While the patient lies still in an appropriate position, the sonographer applies the transducer to a predetermined imaging window on the patient's body. The transducer must be positioned at the correct location and in the correct orientation for the selected imaging window for it to send the ultrasound signals at the proper angle so as to obtain clear and accurate cardiac images.

To place the probe in the proper position, the sonographer must maintain control over the probe throughout the echocardiograph procedure. This often requires the sonographer to apply a large gripping force to the probe casing. Two techniques are commonly used. Left-handed scanning calls for holding the ultrasound probe with the left hand while manipulating the ultrasound imaging system controls with the right hand. Conversely, right-handed scanning calls for using the right hand to control the ultrasound probe while manipulating the imaging system with the left hand. Typically, a right-handed sonographer is positioned behind the horizontally-positioned patient. The sonographer must reach completely around the right side of the patient to properly position the ultrasound probe at one of the ultrasound imaging windows. The gripping force that must be applied by the sonographer to push and hold the probe in the proper location and orientation is significant in such an awkward position. In other situations, the sonographer may have to work in environments even more awkward, such as operating rooms, intensive care units, etc.

In addition, a large percentage of patients on which echocardiography is performed tend to be obese. With such patients, the sonographer must apply a significant gripping force while maneuvering the probe despite layers of fat. Furthermore, the use of coupling gel interferes with the sonographers' capability to securely hold and control the ultrasound probe when the coupling gel migrates from the acoustic path onto the handle surfaces.

It is not uncommon for the sonographer to repeatedly perform procedures to insure that the images that were obtained were accurate representations of the cardiac condition and not artifacts due to improper placement or orientation of the probe. Therefore, occupational injuries to the sonographer may occur due to the continual application of a significant gripping force to the ultrasound probe while performing many such procedures throughout a given time period. Such occupational injuries can increase the cost and decrease the availability of the procedure.

Conventional probes generally have surface features to enable the sonographer to establish the proper orientation of the probe. For example, some ultrasound probes have curves, scallops or ridges, while other probes have a localized feature such as a line, rib, flute, button or some other feature on one side of the transducer.

Although the orientation-related features of conventional ultrasound probes may provide some incidental assistance to the sonographer to maintain control over the probe, these features do not provide significant assistance and are ancillary to the purpose of establishing proper orientation of the probe.

What is needed, therefore, is a means for assisting the sonographer in controlling the ultrasound probe in various operating scenarios, including different relative positions of the sonographer and the patient and the presence of coupling gel. The resulting ultrasound probe should also accommodate all traditional viewing windows, regardless of the physical condition of the patient. The probe should be comfortable to hold and easily controllable with minimal gripping force in all of the noted environments to reduce fatigue and the occurrence of occupational injuries.

SUMMARY OF THE INVENTION

The present invention is related to an ultrasound probe grip layer that overcomes the above and other drawbacks of conventional ultrasound imaging probes. In one aspect of the invention, the grip layer is circumferentially formed substantially around a length of a probe housing. Preferably, the grip layer is substantially non-compressible and has a high coefficient of friction when subject to hand forces. Advantageously, this enables an administering sonographer to maintain control over the ultrasound probe during transthoracic and other ultrasound imaging procedures while applying minimal gripping force. Furthermore, the grip layer accommodates all ultrasound viewing windows regardless of the position of the patient, the location of the sonographer relative to the patient and whether the sonographer uses a right- or left-handed technique to perform the echocardiographic procedure. Preferably, the grip layer is circumferentially formed completely around a predetermined length of the ultrasound imaging probe housing.

In one embodiment, the grip layer is joined to the probe housing so as to form a gas- and liquid-impermeable seal between the grip layer and housing. The impermeable seal enables the ultrasound probe to withstand repeated applications of autoclaving, liquid and chemical disinfectants and other high-speed, high-pressure sterilization procedures without compromising the electrical integrity of the internal components of the probe. The surface of the grip layer is preferably flush with the surface of the housing, resulting in a continuously smooth casing surface that minimizes the accumulation of cleaning solvents, coupling gel and contaminants in any junction between the grip layer and the probe housing. In addition, this enables the resulting casing to be easily wiped off between ultrasound imaging procedures.

In one embodiment, the probe housing has an inner housing extending a substantial length of the probe and an interlocking rear housing for securing a cable assembly to the ultrasound probe. The grip layer is mechanically interlocked between the inner and rear housings to form the impermeable barrier between the grip layer and the housings. The mechanical interlocking of the housing and grip layer results in the grip layer being permanently joined with the probe housing without adhesives. This also enables the grip layer to remain stationary relative to the probe housing when exposed to axially- and rotationally-applied hand forces during ultrasound imaging procedures.

More specifically, the reduced control-pressure grip layer is preferably a substantially thin, rigid, elastomeric coating having a high coefficient of friction, a high chemical resistance, good cut resistance, and excellent adhesion to the underlying probe housing. The grip layer is preferably a low durometer thermoplastic elastomer.

In another aspect of the present invention, an ultrasound probe having an external casing is disclosed. The probe casing includes a housing generally defining a shape of the ultrasound probe and a substantially rigid grip layer circumferentially formed substantially around a length of the housing. The grip layer preferably has a coefficient of friction that is higher than the coefficient of friction of the housing. In one embodiment, the grip layer is secured to the inner housing so as to form a substantially gas- and liquid-impermeable seal between the grip layer and the housing.

The probe housing includes an inner housing extending a substantial length of the probe and a rear housing configured to interlock with a proximal end of the inner housing and to secure a cable assembly to the ultrasound probe. The grip layer is interposed and secured between the rear housing and the inner housing at a proximal end of the grip layer, while the inner housing and grip layer are mechanically interlocked at a distal end of the grip layer. Preferably, the surface of the grip layer at its distal end and the immediately adjacent surface of the inner housing not covered by the grip layer are flush so as to form a continuously smooth casing surface. The continuously smooth casing surface is substantially impenetrable by cleaning solvents, coupling gel and contaminants, enabling the probe casing to withstand repeated sterilization procedures without compromising the electrical integrity of the ultrasound probe. In addition, the resulting casing minimizes the accumulation of debris, gel and other contaminants at the junction between the grip layer and inner housing. The grip layer is preferably insert molded onto the inner housing. The housing may be formed from metals, plastics or other materials.

In another aspect of the invention a method for forming a reduced control-pressure grip layer on an ultrasound probe is disclosed. The method includes the steps of forming a housing generally defining a shape of the ultrasound probe, the housing providing a base substrate; and insert molding a grip layer onto the base substrate of the housing. In one embodiment, the forming step includes injection molding the housing of the ultrasound probe.

Further features and advantages of the present invention, as well as the structure and operation of various embodiments of the present invention, are described in detail below with reference to the accompanying drawings. In the drawings, like reference numbers indicate like or functionally similar elements. Additionally, the left-most one or two digits of a reference numeral identifies the drawings in which the reference numeral first appears.

BRIEF DESCRIPTION OF THE DRAWINGS

This invention is pointed out with particularity in the appended claims. The above and further advantages of this invention may be better understood by referring to the following description when taken in conjunction with the accompanying drawings, in which:

DETAILED DESCRIPTION

Figure 1:
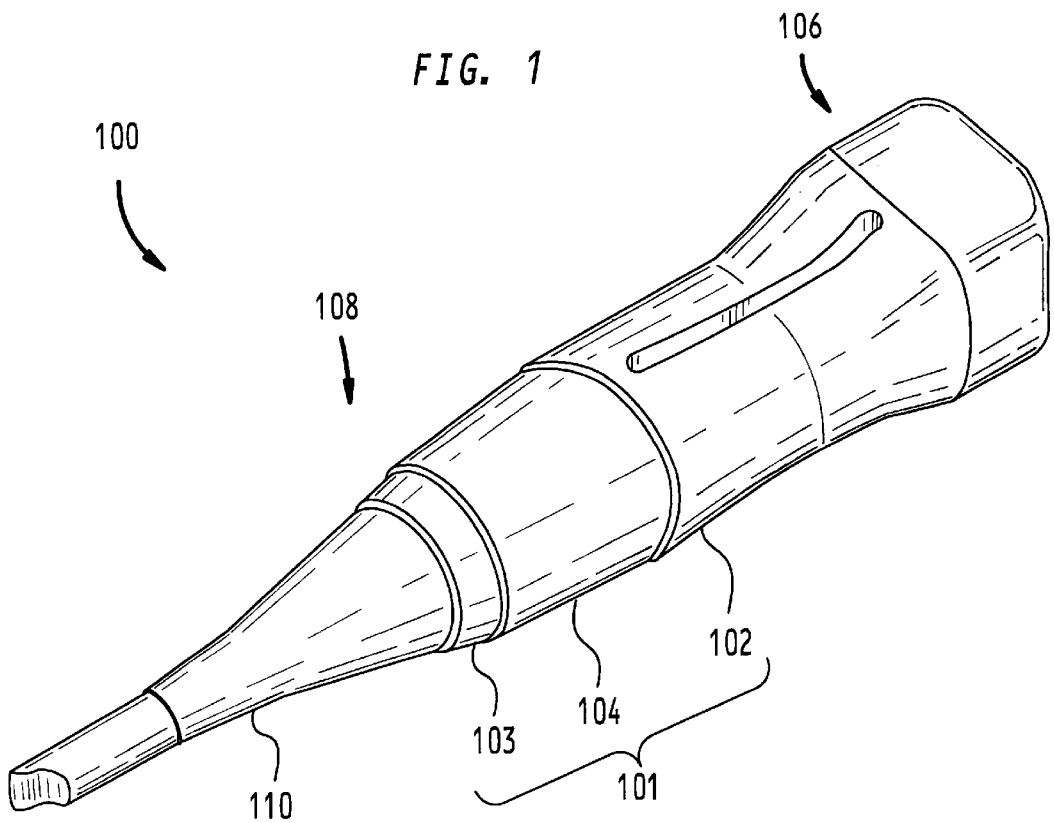
FIG. 1 is a perspective view of one embodiment of the ultrasound probe of the present invention.
Figure 2A:
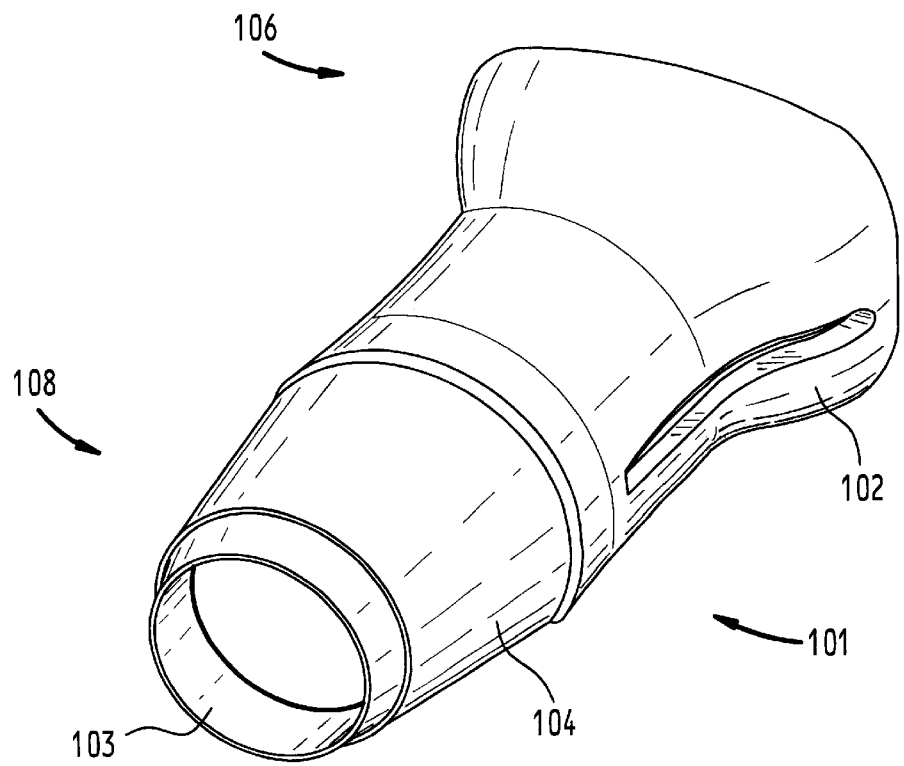
FIG. 2A is a perspective view of one embodiment of the ultrasound probe casing of the present invention.
Figure 2B:
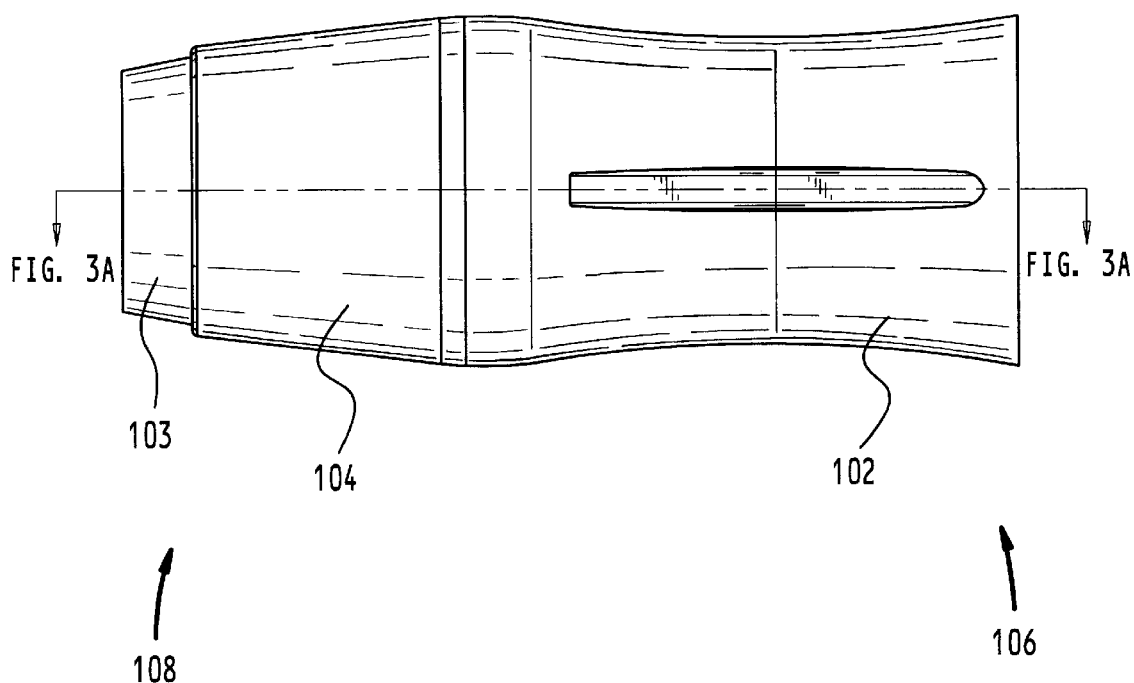
FIG. 2B is a side view of the ultrasound probe casing of the present invention illustrated in FIG. 2A.
Figure 2C:
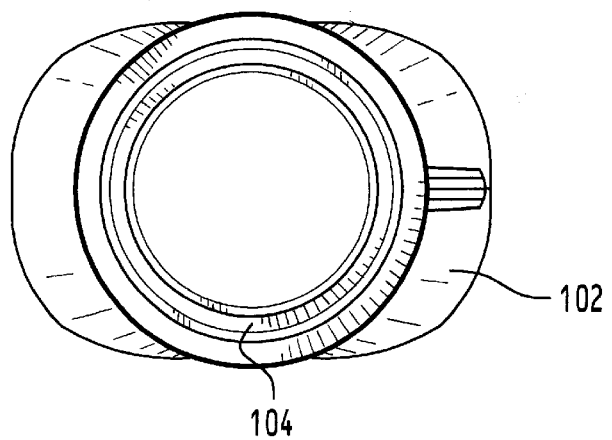
FIG. 2C is a rear view of the ultrasound probe casing of the present invention illustrated in FIG. 2A.

FIG. 1 is a perspective view of one embodiment of the ultrasound probe of the present invention. The probe 100 includes a probe casing 101 which houses well-known internal components of the probe 100. The probe casing 101 is constructed in accordance with one embodiment of the present invention to include an inner housing 102, a rear housing 103 and a grip layer 104. FIG. 2A is a perspective view of one embodiment of the ultrasound probe casing 101 of the present invention. FIG. 2B is a side view and FIG. 2C is a rear view of the ultrasound probe casing 101 illustrated in FIG. 2A.

At a nose or distal end 106 of the ultrasound probe 100 is a lens of the transducer (not shown) which is placed against a patient's body to obtain ultrasound images. Attached to a tail or proximal end 108 of the probe 100, is a cable assembly 110 for carrying signals between the probe 100 and an ultrasound imaging system (not shown). The distal end 106 and proximal end 108 will be used herein to refer to that portion of the inner housing 102, rear housing section 103 and grip layer 104 that are towards the nose and tail, respectively, of the probe 100.

The grip layer 104 is formed circumferentially around a substantial portion of a length of the inner housing 102. Preferably, the grip layer 104 is formed completely around the perimeter of the inner housing 102. It is also preferred that the grip layer 104 is substantially non-compressible and has a high coefficient of friction. As shown in FIG. 1, the grip layer 104 is preferably formed along a predetermined length of the probe 100 towards the proximal end of the inner housing 102 to accommodate a typical grasp by a sonographer. However, it shall be noted that other arrangements and configurations are possible depending on, for example, the anticipated operating environment in which the ultrasound probe will be used.

Advantageously, the grip layer of the present invention enables an administering sonographer to maintain control over the ultrasound probe during transthoracic and other ultrasound imaging procedures while applying minimal gripping force. As a result, the sonographer is required to use less gripping force throughout the procedure, preventing fatigue and enabling the sonographer to perform ultrasound imaging procedures for longer periods of time without loss of control and without incurring occupational injuries. Importantly, the grip layer 104 enables the sonographer to efficiently obtain accurate ultrasound images from all ultrasound viewing windows regardless of the position of the patient, the location of the sonographer relative to the patient, and whether the sonographer uses right- or left-handed techniques.

Figure 3A:
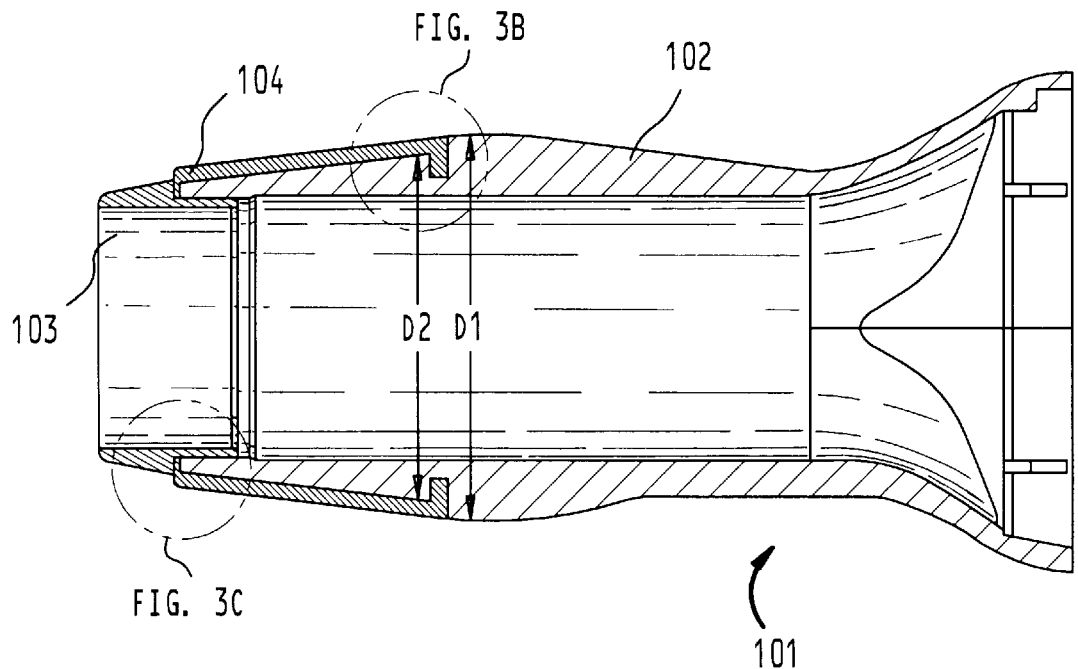
FIG. 3A is a cross-sectional view of the ultrasound casing taken along the FIG. 3A section lines in FIG. 2B.
Figure 3B:
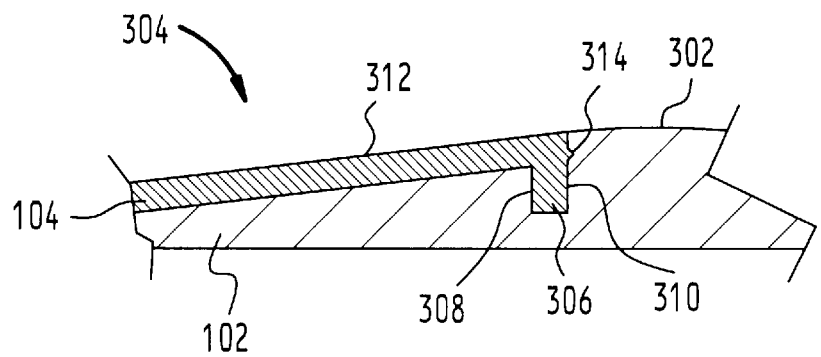
FIG. 3B is a cross-sectional view of the indicated portion of the ultrasound probe casing wherein the distal end of the friction grip is joined to the inner housing 102.
Figure 3C:
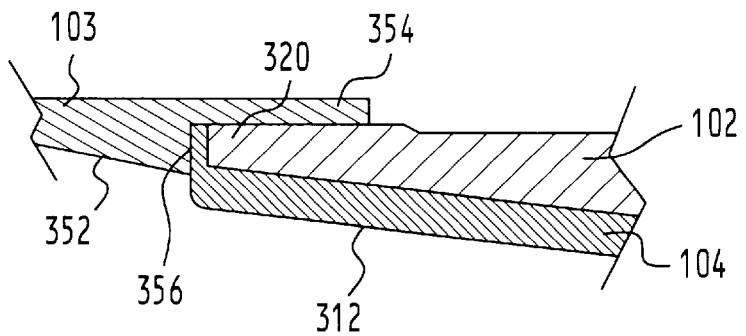
FIG. 3C is a cross-sectional view of the indicated portion of the ultrasound probe casing wherein the proximal end of the friction grip is joined to the inner housing.

FIG. 3A is a cross-sectional view of the casing 101 taken along the FIG. 3A is section lines in FIG. 2B. FIG. 3B is an enlarged cross-sectional view of the indicated portion of the ultrasound probe casing 101 wherein the distal end of the friction grip 104 is joined to the inner housing 102. FIG. 3C is an enlarged cross-sectional view of the indicated portion of the ultrasound probe casing wherein the proximal end of the grip layer 104 is joined to both the inner housing 102 and rear housing section 103. In one embodiment, the grip layer 104 is joined to the inner housing 102 and rear housing section 103 so as to form a gas- and liquid-impermeable seal between the grip layer 104 and the housings 102 and 103.

Referring to FIG. 3B, the grip layer 104 and the inner housing 102 are interlocked to form an impermeable junction between the grip layer 104 and inner housing 102. The portion of the probe casing 101 that includes the grip layer 104 has a stepped surface 302 at the distal end of the grip layer 104, and is tapered towards the proximal end of the probe casing 101. The stepped region 304 is defined by a larger inner housing diameter D1 distal to the stepped region 304 and a smaller inner housing diameter D2 proximate to the stepped region 304. At the stepped region 304 a channel 306 is formed around the perimeter of the inner handle 104. In one embodiment, the channel 306 is formed around the entire circumference of the inner handle 104. The formation of the channel 306 defines a shoulder 308 in the inner housing 104. The shoulder 308 prevents the grip layer 104 from being separated from the inner housing 102 when an axial force directed towards the proximal end 108 of the probe casing is applied to the grip layer 104.

The stepped region 304 provides a surface 310 against which the grip layer 104 abuts. This surface 310 prevents the grip layer 104 from traveling in a direction parallel with the housing surface towards the distal end of the probe 100. As a result, the surface 310 prevents the grip layer 104 from separating from the inner housing 102 when an axial force directed towards the distal end 106 of the casing 101 is applied to the grip layer 104.

As shown in FIGS. 3A and 3B, there is a smooth transition from the surface 312 of the grip layer 104 to the surface 302 of the inner housing 102. The surfaces of the grip layer 104 and inner housing 102 are preferably flush to form a continuously smooth casing surface that minimizes the accumulation of cleaning solvents, coupling gel or contaminants at the junction between the grip layer 104 and the inner and rear housings 102 and 103. In addition, this enables the resulting surface of the casing 101 can be easily wiped off between ultrasound imaging procedures. The liquid-tight seal enables the ultrasound probe 100 to withstand repeated applications of autoclaving, liquid and chemical disinfecting and other sterilization methods without compromising the electrical integrity of the probe casing.

To further insure that the casing 101 prevents the penetration of contaminants and cleaning solvents, in one embodiment, a mechanical interlock 314 is formed in the abutting surface 310 of the stepped region 304. The mechanical interlock 314 ensures that the grip layer 104 is mechanically secured to the inner housing 102, and reduces the stress on the bond between the grip layer 104 and the inner housing 102. This also provides a circuitous path between the grip layer 104 and inner housing 102, insuring that no gel or other contaminants work their way between the grip layer 104 and the inner housing 102 during the operational life of the probe 100. In one embodiment, the mechanical interlock 314 is formed using a punch.

FIG. 3C is an enlarged view of the proximal end of the grip layer 104 joined to the inner housing 102 towards the proximal end of the probe casing 100. As shown in FIG. 3C, the grip layer 104 wraps around the edge 320 of the inner housing 102. An interlocking rear housing 103 of the casing 101 has a stepped outer surface 352 forming a radial wall 356 and a ledge 354 having an outside diameter that is less than an inside diameter of the inner housing 102 enabling the ledge 354 to be inserted into the inner housing 102. The grip layer 104 is secured between the radial wall 356 of the rear housing 103 and the edge 320 of the inner housing 102 when the rear housing 103 is fully inserted into the inner housing 102.

To provide a tapered surface while providing sufficient volume to hold the internal components of the probe 100, the inner housing 102 is preferably thinner towards the proximal end of the probe 100. Accordingly, interposing the grip layer 104 between the rear housing 103 and the inner housing 102 is a preferred approach at the proximal end 108 of the probe 100. Forming a channel similar to channel 306 at the proximal end 108 of the inner housing 102 may reduce the strength of certain configurations of the inner housing 102 due to is relative thinness.

Importantly, the edge of the grip layer 104 at its proximal end is not exposed. This prevents the grip layer 104 from being lifted from the inner housing 102, which may cause unsanitary conditions. In addition, the ledge 354 extends a substantial distance into the interior of the inner housing 102 past the edge 320. An advantage of this arrangement is that it forms a gas- and water-impermeable seal at the junction between the grip layer 104 and both the inner housing 102 and rear housing section 103. Accordingly, this arrangement prevents gel, solvents and contaminants from penetrating the casing 101.

As noted, the seamless, gas- and liquid-impenetrable casing 101 prevents entry of water, bacteria, particles, etc. into the ultrasound probe 100. Advantageously, the casing 101 enables the ultrasound probe 100 to withstand repeated cycles of autoclaving, gas sterilization, ethylene oxide (ETO) liquid disinfection and other commonly used methods of sterilization. Other sterilization techniques have been recently developed in response to the continuing economic pressure to reduce the amount of time medical products require for disinfection. Such sterilization techniques include, for example, application of a combination of hot water and various chemicals. The ability of the present invention to withstand repeated applications of such sterilization techniques enables the ultrasound probe 100 to be used with patients who have an infectious disease without increasing the risk of exposure to the sonographer or other patients.

Importantly, due to the seamless configuration of the casing 101, the ultrasound probe 100 may be easily wiped clean with water or chemicals without damage to the internal components of the probe. In many environments, this casual cleaning, such as by wiping-off the probe with a tissue or an alcohol swab, is often performed multiple times during and after the performance of echocardiographic procedures. The ability to prevent the accumulation of debris and solvents on the casing 101 during the repeated use and subsequent cleaning of the probe casing results in a greater availability of the ultrasound probe 110. As a result, the grip layer 104 provides the above advantages without compromising the electrical integrity of the probe case 101.

The inner housing 102 and rear housing 103 provide a base substrate which can be formed from the same or different conventional grip base substrate materials. Such materials include metals such as aluminum, iron and alloys thereof or plastics which are thermoset or thermoplastic, including plastics such as glass reinforced polyesters. Other plastics including reinforced or unreinforced epoxies, polyethylenes, polybutylenes, polypropylenes, vinyls and known grip base substrate materials can also be used.

Preferably the grip layer 104 has low durometer as, for example, Shore A3–65, ASTM D2240; high chemical resistance as, for example, resistance without substantial deterioration for thirty days to materials encountered in the use environment which include isopropanol, glutaraldehyde, Clorox (5% sodium hypochlorite), peracetic acid; good tear resistance as, for example, tear strength of greater than 300 lb/in, ASTM D1922; and, excellent adhesion to the underlying base substrate as, for example, peel strengths of greater than 5 pli (lb. per linear inch), ASTM D429-81. Preferably, the grip layer 104 is a polymeric thermoplastic elastomer; that is, a thermoplastic containing rubber domains. Such materials inherently provide low durometer, providing a grip layer 104 having high friction characteristics to allow for good control of the probe 100 with maximized comfort and control to the user's hand.

A preferred material for use as the reduced control pressure grip layer 104 is available from J. Von, a company of Leominster, Mass., under its trade name Hercuprene™. Hercuprene™ S2954-BX2, for example, has excellent properties for use as the grip layer of the transducer casing of this invention. This material has a Shore A hardness of 47, ASTM, D-2240, a density of 0.99G/CC, ASTM, D-792, a tensile modulus of 127 psi at 100%, ASTM, D-412, an elongation of 783% at ASTM, D-412, a Taber abrasion of 850MG LOSS (H-18, 1KC) ASTM, D-1044. The material can be molded into desired layers at injection molding temperatures of 221° C. with mold temperatures of 50° C. or at other temperatures and conditions known to the art. In some cases, the layer can be formed extremely thin and deposited after a coating operation as known in the art. Preferably, insert injection molding procedures are used to achieve the desired grip layer thickness. In alternative embodiments, coating and other laminating, molding and casting procedures of all types can be used for forming the reduced control pressure grip layer 104 of the present invention.

While the grip layer 104 preferably has low durometer, high chemical resistance, good tear resistance and excellent adhesion, it should be understood that in some cases the grip layer 104 can have only two or more of these properties and still provide excellent advantages. For example, the above-noted property of low durometer can be obtained from certain polyurethanes, polyesters, silicones, polyvinyl chlorides and natural or synthetic rubbers, while the noted chemical resistance may also be found in certain polyolefins, silicones, and the like, and the noted cut resistance may be present in certain polyurethanes, polyesters and rubbery materials.

It should also be understood that other materials may be used. For example, in one embodiment, blends providing properties of elastomers and plastics are used. Elastomers for blends include, for example, EPDM or Santoprene™ with oxidized, epoxidized rubber or anhydride additives; and thermoplastic elastomer or vulcanized rubber blended into plastics. (Santoprene is a trademark of Advanced Elastomers, Inc.) Thermoplastic elastomers for elastomer/plastic blends that may also be used for the grip layer include, for example, Santoprene/rubber/nylon, butyl, EPDM, poly-trans-pentenamer, natural rubber, butadiene rubber, SBR, ethylene-vinyl acetate rubber, acrylate rubber, chlorinated polyethylene, neoprene and nitrile rubber. Vulcanized rubber-plastic blends can be used as thermoplastic elastomer grip materials, as well. Dynamically vulcanized rubbers are processed as thermoplastics with the use of curative systems in the mixing stages. Plastics in the elastomer/plastic blends include polypropylene, polyethylene, polystyrene, ABS, SAN, polymethyl methacrylate, polybutylene terephthalate, polyamides and polycarbonates.

In a specific embodiment of this invention, a grip layer 104 is formed on a handle base substrate by the following procedure: (1) a preformed handle base substrate having a bore diameter of approximately 18 mm is placed in a mold leaving an insert portion facing a molding cavity; and (2) injection molding is carried out at a temperature of 390–430° F. for a predetermined mold clamp time of approximately 3 seconds at approximately 4200 psi. Grip layer material is introduced into the mold cavity and an insert such as 102 is formed with a thickness of approximately 0.020 inches.

Probe casings made in accordance with this invention having a thickness of approximately 0.5 mm satisfy each of the minimum tests outlined above for cut resistance, adhesion, chemical resistance and low durometer.

While various embodiments of the present invention have been described above, it should be understood that they have been presented by way of example only, and not limitation. For example, in one embodiment, the rear housing 103 is color coded to identify different types or models of the ultrasound probe 100. Thus, the breadth and scope of the present invention are not limited by any of the above described exemplary embodiments, but are defined only in accordance with the following claims and their equivalents.

What is claimed is:

1. A grip layer circumferentially formed substantially around, and mechanically interlocked with a region of an exterior surface of an ultrasound imaging probe housing wherein said exterior surface has formed therein a stepped recess including at least one channel whereat said recess has a smaller cross-sectional diameter than other regions of the recess, said channel defining a surface substantially orthogonal to said exterior surface, said grip formed within said recess so as to mechanically interlock with said exterior surface of the ultrasound imaging probe.

2. The grip layer of claim 1, wherein said grip layer is substantially non-compressible when subject to hand forces.

3. The grip layer of claim 1, wherein said grip layer is joined to said housing so as to form a substantially gas- and liquid-impermeable seal between said grip layer and said housing.

4. The grip layer of claim 3, wherein said grip layer is formed on said housing through the performance of an insert molding process.

5. The grip layer of claim 1, wherein said grip layer has a high coefficient of friction, high chemical resistance and good cut resistance.

6. The grip layer of claim 5, wherein said grip layer has a low durometer in the range of Shore A3-65, ASTM D2240.

7. The grip layer of claim 5, wherein said high chemical resistance includes resistance without substantial deterioration for thirty days to materials encountered in the use environment which include isopropanol, glutaraldehyde, Clorox (sodium hypochlorite hydroxide) and peracetic acid.

8. The grip layer of claim 5, wherein said good cut resistance comprises tear strength of greater than 300 lb/in, ASTM D1922.

9. The grip layer of claim 1, wherein said grip layer is a thermoplastic, an elastomer, or a thermoplastic elastomer.

10. The grip layer of claim 1, wherein said grip is formed completely around said length of said ultrasound imaging probe housing.

11. An ultrasound probe having an external casing comprising:
 a housing generally defining a shape of the ultrasound probe; and
 a substantially non-compressible grip layer circumferentially formed substantially around said housing over a length of said housing, wherein said grip layer is mechanically interlocked with said housing and has a coefficient of friction that is higher than a coefficient of friction of said housing.

12. The probe of claim 11, wherein said grip layer is seamlessly joined to said housing so as to form a gas-and liquid-impermeable seal between said grip layer and said housing.

13. The probe of claim 11, wherein said housing comprises:
 an inner housing extending a substantial length of the probe; and
 a rear housing configured to interlock with a proximal end of said inner housing;
 wherein said grip layer is formed on said inner housing and secured between said rear housing and said inner housing at a proximal end of said grip layer, and
 wherein said inner housing and said grip layer are mechanically interlocked at a distal end of said grip layer.

14. The probe of claim 13, wherein
 said grip layer is joined to said inner housing so as to form a gas- and liquid-impermeable seal between said grip layer and said inner housing.

15. The probe of claim 13, wherein said distal end of said grip layer and said inner housing form a substantially smooth casing surface that is substantially impenetrable by cleaning solvents, coupling gel and contaminants.

16. The grip layer of claim 11, wherein said grip layer is formed completely around said length of said ultrasound imaging probe housing.

17. The probe of claim 11, wherein said housing is formed from metals.

18. The probe of claim 11, wherein said housing is formed from plastics.

19. The probe of claim 13, wherein said distal end of said grip layer and said inner housing form a substantially smooth casing surface that is substantially impenetrable by cleaning solvents, coupling gel and contaminants.

20. The grip layer of claim 1, wherein said housing has formed therein first and second channels defining distal and proximal boundaries of said length of said probe housing.

21. An ultrasound probe having an external casing comprising:
 a housing generally defining a shape of the ultrasound probe, including,
  an inner housing extending a substantial length of the probe, and
  a rear housing configured to interlock with a proximal end of said inner housing; and
 a substantially non-compressible grip layer circumferentially formed substantially around said housing over a length of said housing, wherein said grip layer is formed on said inner housing and secured between said rear housing and said inner housing at a proximal end of said grip layer, and wherein said inner housing and said grip layer are mechanically interlocked at a distal end of said grip layer.

22. The probe of claim 21, wherein said grip layer is substantially seamlessly joined to said inner housing.

23. The probe of claim 21, wherein
 said grip layer is joined to said inner housing so as to form a gas- and liquid-impermeable seal between said grip layer and said inner housing.

* * * * *